United States Patent [19]

Showalter et al.

[11] Patent Number: 5,061,791

[45] Date of Patent: Oct. 29, 1991

[54] 4-BROMO-4'-DEMETHYLEPIPODOPHYL-LOTOXIN DERIVATIVES

[75] Inventors: Howard D. H. Showalter; Roy T. Winters, both of Ann Arbor, Mich.

[73] Assignee: Warner-Lambert Company, Morris Plains, N.J.

[21] Appl. No.: 407,662

[22] Filed: Sep. 19, 1989

Related U.S. Application Data

[63] Continuation-in-part of Ser. No. 287,235, Dec. 21, 1988, abandoned, which is a continuation-in-part of Ser. No. 262,642, Oct. 26, 1988, abandoned.

[51] Int. Cl.$^5$ .................... C07H 11/04; C07H 15/00
[52] U.S. Cl. ................... 536/17.4; 536/17.2; 536/17.5; 536/17.6; 536/17.9; 536/18.1; 549/298
[58] Field of Search ............... 536/17.9, 17.6, 18.1, 536/17.2, 17.4, 17.5; 549/298

[56] References Cited

U.S. PATENT DOCUMENTS

| | | | |
|---|---|---|---|
| 3,524,844 | 8/1970 | Keller-Juslen et al. | 536/18.1 |
| 4,556,654 | 12/1985 | Showalter et al. | 514/222 |
| 4,564,675 | 1/1986 | Kurabayashi et al. | 536/18.1 |
| 4,604,390 | 8/1986 | Elslager et al. | 514/222 |
| 4,609,644 | 9/1986 | Nemec | 536/18.1 |
| 4,912,204 | 3/1990 | Ohnuma et al. | 536/18.1 |

FOREIGN PATENT DOCUMENTS

| | | |
|---|---|---|
| 3122484 | 7/1985 | Australia . |
| 0162701 | 11/1985 | European Pat. Off. . |
| 0226202 | 6/1987 | European Pat. Off. . |
| 63-10789 | 1/1988 | Japan . |
| 63-23884 | 2/1988 | Japan . |
| 8501123 | 11/1985 | PCT Int'l Appl. . |

OTHER PUBLICATIONS

Synthesis and Biological Evaluation of Antitumor Analogues of Podophyllotoxin and α-Peltatin (1986) Lee Scott Thurston-pp. 42, 45, 46.
Studies on Lignan Lactone Antitumor Agents, I, Saito et al., Chem. Pharm. Bull. 34(9), 3733-3740 (1986).
Studies on Lignan Lactone Antitumor Agents, II, Saito et al., Chem. Pharm. Bull. 34(9), 3741-3746 (1986).
Derwent Abstract No. 89-153953/21 for JO 1093-58-9-A.
Journal of Natural Products, Kuo-Hsiung Lee et al., vol. 52, No. 3, pp. 606-613, May-Jun. 1989.
Studies on Lignan Lactone Antitumor Agents. V. Saito et al., Bull. Chem. Soc. Jpn., vol. 61, No. 2, 2493-2497 (1988).
Derwent Abstract No. 88-068417/10 for J6 3023-88-4-A.

*Primary Examiner*—Johnnie R. Brown
*Assistant Examiner*—Elli Peselev
*Attorney, Agent, or Firm*—Joan Thierstein

[57] ABSTRACT

Preparation of 4-bromo-4'-demethylepipodophyllotoxin by reacting podophyllotoxin with hydrogen bromide at about −20° C. New antitumor compounds of the formula:

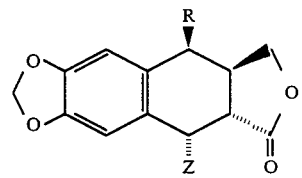

wherein R is A—(CH$_2$)$_n$[A(CH$_2$)$_n$]$_m$(CHAH)$_p$—Q or

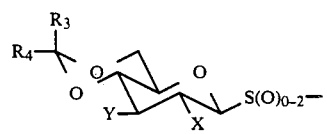

each A, independently, is O, S, SO or SO$_2$; n is an integer from 1 to 6, except when n and p, taken together, are zero, then n is 2 to 6; n is 0, 1, or 2; p is 0, 1, or 2; Q is H, alkyl from 1 to 6 carbon atoms which may be substituted with an NR$_1$R$_2$ group wherein each R$_1$ and R$_2$, independently, is selected from the group of H, alkyl containing 1 to 6 carbon atoms which may be substituted with OH, alkanoyl containing 1 to 6 carbon atoms, or R$_1$ and R$_2$ are interconnected and together with the N to which they are connected form an N heterocyclic ring of 5 to 6 carbon atoms; R$_3$ is hydrogen, and R$_4$ is an alkyl, alkenyl, cycloalkyl, 2-furyl, 2-thienyl, aryl, aralkyl, and aralkenyl, wherein the aromatic ring may optionally be substituted, preferentially by one or more of hydroxyl, alkyl, alkoxy, nitro, or halogen radicals. R$_3$ and R$_4$ together with the carbon atom to which they are attached may form a saturated cycloaliphatic ring having 5 or 6 carbon atoms; each X and Y, individually, is OH or NR$_6$R$_7$ wherein R$_6$ and R$_7$, independently, is H, alkyl containing 1 to 6 carbon atoms or one of R$_6$ and R$_7$ is acyl; and Z is

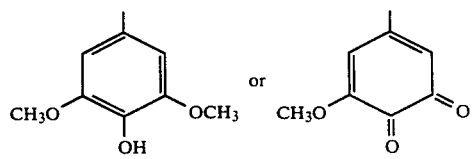

Novel process for the preparation of the novel compounds or analogs thereof having advantageous stereoselection using alkyltin thiolates, preferably with selected solvents.

20 Claims, No Drawings

4-BROMO-4'-DEMETHYLEPIPODOPHYL-LOTOXIN DERIVATIVES

CROSS-REFERENCE TO RELATED APPLICATIONS

This is a continuation-in-part of copending application Ser. No. 287,235, filed Dec. 21, 1988, now abandoned, which is a continuation-in-part of application Ser. No. 262,642, filed Oct. 26, 1988, now abandoned, and entitled "Method for Producing 4-Bromo-4'Demethylepipodophyllotoxin and New Derivatives Thereof".

TECHNICAL FIELD

The present invention is concerned with an improved process for producing 4-bromo-4'-demethylepipodophyllotoxin. The process of the present invention provides for increased yields along with higher purity of the desired 4-bromo-4'-demethylepipodophyllotoxin.

In addition, the present invention is concerned with new compounds that are derived from the 4-bromo-4'-demethylepipodophyllotoxin. These new compounds are especially useful as antitumor agents.

BACKGROUND ART

The antineoplastic activity of podophyllotoxin is well documented. However, since it is extremely toxic, it has rarely been used in treating humans. Accordingly, various derivatives of podophyllotoxin have been developed over the years in an attempt to obtain antineoplastic compounds with reduced toxicity. For instance, etoposide and teniposide have reduced toxicity and have exhibited antineoplastic activity against certain tumors, including small-cell carcinoma of the lung, acute leukemia, malignant lymphoma, and testicular cancer.

In the preparation of various derivatives of podophyllotoxin it has been suggested, as exemplified by U.S. Pat. No. 3,524,844 to Keller-Juslen, et al., to prepare 4-bromo-4'-demethylepipodophyllotoxin by reacting podophyllotoxin with hydrogen bromide. The reaction suggested therein is carried out at $-20°$ C. to $+40°$ C. and preferably at $0°$ C. and employing solutions of, for example, ethylene chloride saturated with hydrogen bromide gas.

In addition, a number of other derivatives of podophyllotoxin have been suggested as antitumor agents, including those discussed in Australian Application No. 31224/844 Japanese Kokai No. 63-10780; Japanese Kokai 63-23884; Thurston, *Synthesis and Biological Evaluation of Antitumor Analogues of Podophyllotoxin and α-Peltatin*, University of North Carolina, 1986; Saito, et al., "Studies of Lignan Lactone Antitumor Agents. I. Synthesis of Aminoglycosidic Lignan Variants Related to Podophyllotoxin", *Chem Pharm Bull*, 34(9):3733–3740 (1986); and Saito, et al., "Studies in Lignan Lactone Antitumor Agents II Synthesis of N-Alkylamino and 2,6-Dideoxy-2-Aminoglycosidic Lignan Variants Related to Podophyllotoxin", *Chem Pharm Bull*, 34(9):3741–3746 (1986). Additionally, Japanese Patent Application 1093-589A disclosed in Derwent Abstract No. 89-153953/21 and Lee, et al., *J of Natural Products*, 52(3):606–6113 (May–June 1989), define derivatives of 4'-demethylepipodophyllotoxin as antitumor agents.

Furthermore, various processes have been suggested for producing certain derivatives of podophyllotoxin such as in U.S. Pat. No. 4,564,675 and European Patent Publications 0162701 and 226202.

SUMMARY OF INVENTION

In accordance with the present invention, 4-bromo-4'-demethylepipodophyllotoxin can be produced in increased yields along with enhanced purity as compared to prior art methods of preparation. In particular, according to the present invention, increased yields of high purity 4-bromo-4'-demethylepipodophylotoxin are obtained by reacting podophyllotoxin with hydrogen bromide It is critical to the success of the present invention that the hydrogen bromide be employed as an anhydrous solution of hydrogen bromide in an inert solvent in concentrations of about 2 to about 3 molar, as contrasted to the saturated solution described in U.S. Pat. No. 3,524,844. The reaction of the present invention must be carried out at temperatures of about $-30°$ C. to about $-10°$ C.

The 4-bromo-4'-demethylepipodophyllotoxin obtained by the present invention can be used to prepared known antitumor derivatives of podophyllotoxin, including those disclosed in U.S. Pat. No. 3,524,844, as well as new antitumor compounds. These new antitumor compounds that form another aspect of the present invention are represented by the formula:

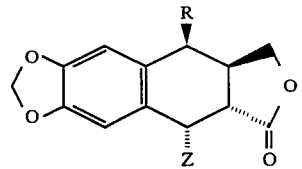

wherein R is A—$(CH_2)_n[A(CH_2)_n]_m(CHAH)_p$—Q or

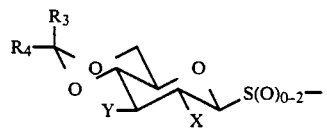

each A, independently, is O, S, SO, or $SO_2$; n is an integer from 1 to 6, except when m and p, taken together, are zero, then n is 2 to 6; m is 0, 1, or 2; p is 0, 1, or 2; Q is H, alkyl from 1 to 6 carbon atoms which may be substituted with an $NR_1R_2$ group wherein each $R_1$ and $R_2$, independently, is selected from the group of H, alkyl containing 1 to 6 carbon atoms which may be substituted with OH, alkanoyl containing 1 to 6 carbon atoms, or $R_1$ and $R_2$ are interconnected and together with the N to which they are connected form an N heterocyclic ring of 5 to 6 carbon atoms; $R_3$ is hydrogen, and $R_4$ is an akyl, alkenyl, cycloalkyl, 2-furyl, 2-thienyl, aryl, aralkyl, and aralkenyl, wherein the aromatic ring may optionally be substituted, preferentially by one or more of hydroxyl, alkyl, alkoxy, nitro, or halogen radicals. $R_3$ and $R_4$ together with the carbon atom to which they are attached may form a saturated cycloaliphatic ring having 5 or 6 carbon atoms; each X and Y, individually, is OH, or $NR_6R_7$, wherein $R_6$ and $R_7$ is independently alkyl containing 1 to 6 carbon atoms or H, or one of $R_6$ and $R_7$ is acyl; and Z is

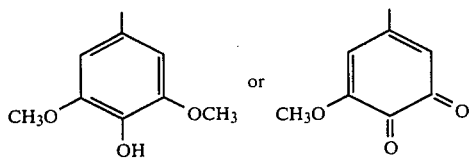

It is now also found that the reaction of the 4-bromo-4'-demethylepipodophyllotoxin is unexpectedly advantageous as described above for use to obtain the novel compounds of the present invention when the metallic salt of the above description is a tri-n-butyltin salt.

Thus, the present invention is also a process for the preparation of a compound of the formula

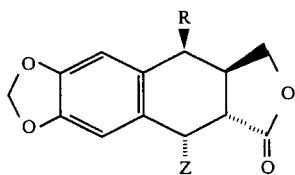

wherein R is $A_1$—$(CH_2)_n[A(CH_2)_n]_m(CHAH)_p$—Q or

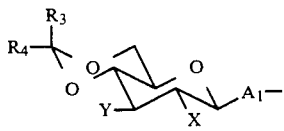

wherein each A, independently, is O, S, SO, or $SO_2$; $A_1$, independently, is O or S; n is an integer from 1 to 6, except when m and p, taken together, are zero, then n is 2 to 6; m is 0, 1, or 2; p is 0, 1, or 2; Q is H, alkyl from 1 to 6 carbon atoms which may be substituted with an $NR_1R_2$ group wherein each $R_1$ and $R_2$, independently, is selected from the group of H, alkyl containing 1 to 6 carbon atoms which may be substituted with OH, alkanoyl containing 1 to 6 carbon atoms, or $R_1$ and $R_2$ are interconnected and together with the N to which they are connected form an N heterocyclic ring of 5 to 6 carbon atoms; $R_3$ is hydrogen, and $R_4$ is an alkyl, alkenyl, cycloalkyl, 2-furyl, 2-thienyl, aryl, aralkyl, and aralkenyl, wherein the aromatic ring may optionally be substituted, preferentially by one or more of hydroxyl, alkyl, alkoxy, nitro, or halogen radicals. $R_3$ and $R_4$ together with the carbon atom to which they are attached may form a saturated cycloaliphatic ring having 5 or 6 carbon atoms; each X and Y, individually, is OH or $NR_6R_7$, and Z is

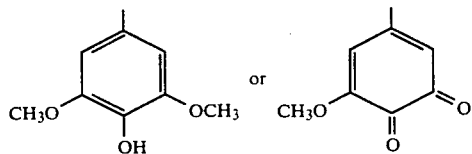

wherein $R_6$ and $R_7$ is independently alkyl containing 1 to 6 carbon atoms or H, or one of $R_6$ and $R_7$ is acyl; comprising a reaction of the 4-bromo-4'-demethylepipoophyllotoxin with a compound of the formula $RA_1SnBu_3$ wherein R and $A_1$ are as defined above and $Bu_3$ is tri-n-butyl.

In other words, the novel process using a tri-n-butyltin salt can be used to prepare the novel compounds of the present invention as well as compounds analogous to the novel compound of the present invention but which are known. Specifically, the known compounds which can be prepared by the present process are analogous to the compounds of the formula I but differ in that the substituent comparable to R is defined as follows:

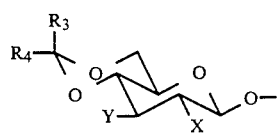

BEST AND VARIOUS MODES FOR CARRYING OUT INVENTION

It has been found, according to the present invention, that increased yields of high purity 4-bromo-4'-demethylepipodophyllotoxin are obtained by reacting podophyllotoxin with an anhydrous solution of hydrogen bromide in an inert solvent. It is critical to the success of the present invention that the concentration of the hydrogen bromide in the solvent be from about 2 to about 3 molar, typical of which is about 2.3 molar.

The inert solvents employed include the halogenated hydrocarbons and ethers. Suitable halogenated hydrocarbons include ethylene chloride, 1,2-dichloroethane, chloroform, and methylene chloride, and preferably 1,2-dichloroethane. The preferred ethers are dialkyl ethers such as diethyl ether. In the most preferred aspects of the present invention, mixtures of the halogenated hydrocarbon and an ether are employed. Usually, the mixtures contain about 5 to about 50 volume percent of the ether and about 95 to about 50 volume percent of the halogenated hydrocarbon.

The podophyllotoxin is usually present in concentrations of about 0.1 to about 0.5 molar, and preferably about 0.2 to about 0.3 molar.

The reaction is carried out at temperatures of about −30° C. to about −10° C., and preferably at about −20° C. The reaction usually takes about 4 to about 10 days, typically, about 8 days for completion.

Typical yields are about 50% to about 60%.

The novel compounds of the present invention that can be prepared from the 4-bromo-4'-demethylepipodophyllotoxin are represented by the formula

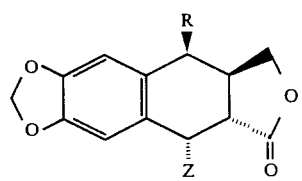

wherein R is $A$—$(CH_2)_n[A(CH_2)_n]_m(CHAH)_p$—Q or

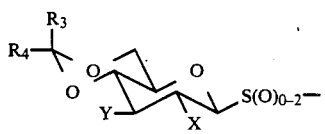

each A, independently, is O, S, SO or $SO_2$; n is an integer from 1 to 6, except when m and p, taken together, are zero, then n is 2 to 6; m is 0, 1, or 2; p is 0, 1, or 2; Q is H, alkyl from 1 to 6 carbon atoms which may be substituted with an $NR_1R_2$ group wherein each $R_1$ and $R_2$, independently, is selected from the group of H, alkyl containing 1 to 6 carbon atoms which may be substituted with OH, alkanoyl containing 1 to 6 carbon atoms, or $R_1$ and $R_2$ are interconnected and together with the N to which they are connected form an N heterocyclic ring of 5 to 6 carbon atoms; $R_3$ is hydrogen, and $R_4$ is an alkyl, alkenyl, cycloalkyl, 2-furyl, 2-thienyl, aryl, aralkyl, and aralkenyl, wherein the aromatic ring may optionally be substituted, preferentially by one or more of hydroxyl, alkyl, alkoxy, nitro, or halogen radicals. $R_3$ and $R_4$ together with the carbon atom to which they are attached may form a saturated cycloaliphatic ring having 5 or 6 carbon atoms; each X and Y, individually, is OH or $R_6R_7$ wherein $R_6$ and $R_7$ is independently alkyl containing 1 to 6 carbon atoms or H, or one of $R_6$ and $R_7$ is acyl; and Z is

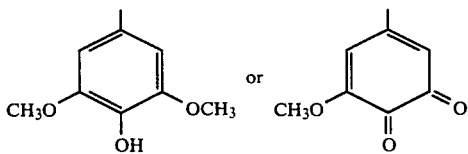

Examples of N-heterocyclic ring of 5 to 6 carbon atoms in the above formula are morpholinyl, thiomorpholinyl, N-alkylpiperazinyl, piperidinyl, and pyrrolidinyl. The rings can also include O and/or S atoms.

Examples of suitable alkyl groups include ethyl, methyl, n-propyl, isopropyl, and n-butyl.

Examples of suitable alkanoyl groups include methanoyl, ethanoyl, and propanoyl

Examples of a suitable aryl group includes phenyl.

Examples of alkenyl groups include ethylene and propylene.

Examples of an aralkyl group is benzyl.

Examples of cycloaliphatic groups are cyclohexyl and cyclopentyl.

Examples of alkoxy groups are methoxy and ethoxy.

Examples of acyl groups are acetyl, propionyl, benzoyl.

Examples of some specific new compounds in accordance with the present invention are:

[5R-(5α,5aβ,8aα,9β)]-5,8,8a,9-tetrahydro-5-(4-hydroxy-3,5-dimethoxyphenyl)-9-[2-[(2-hydroxyethyl)methylamino]ethoxy]furo[3',4':6,7]naphtho[2,3-d]-1,3-dioxol-6(5aH)-one;

[5R-(5α,5aβ,8aα,9β)]-5,8,8a,9-tetrahydro-5-(4-hydroxy-3,5-dimethoxyphenyl)-9-[2-[(4-morpholinyl)ethoxy]furo[3',4':6,7]naphtho[2,3-d]-1,3-dioxol-6(5aH)-one;

[5R-(5α,5aβ,8aα,9β)]-9-[2-(diethylamino)ethoxy]-5,8,8a,9-tetrahydro-5-(4-hydroxy-3,5-dimethoxyphenyl)furo[3',4':6,7]naphtho[2,3-d]-1,3-dioxol-6(5aH)-one;

[5R-(5α,5aβ,8aα,9β)]-9-[2-(diethylamino)ethoxy]-5,8,8a,9-tetrahydro-5-(4-hydroxy-3,5-dimethoxyphenyl)furo[3',4':6,7]naphtho[2,3-d]-1,3-dioxol-6(5aH)-one;

[5R-(5α-5aβ,8aα,9β)]-9-[2-[2-(diethylamino)ethoxy]-ethoxy]-5,8,8a,9-tetrahydro-5-(4-hydroxy-3,5-dimethoxyphenyl)furo[3',4':6,7]naphtho[2,3-d]-1,3-dioxol-6(5aH)-one;

[5S-(5α-5aβ,8aα,9β)]-1-[2-[[5,5a,6,8,8a,9-hexahydro-9-(4-hydroxy-3,5-dimethoxyphenyl)-8-oxofuro3'-4':6,7]-naphtho[2,3-d]-1,3-dioxol-5-yl]oxy]ethyl]-2-pyrrolidinone;

[5R-(5α,5aβ,8aα,9β)]-5,8,8a,9-tetrahydro-5-(4-hydroxy-3,5-dimethoxyphenyl)-9-[[2-(4-morpholinyl)ethyl]thio]furo[3',4':6,7]naphtho[2,3-d]-1,3-dioxol-6(5aH)-one;

[5R-(5α,5aβ,8aα,9β)]-9-[(2,3-dihydroxypropyl)thio]5,8,8a,9-tetrahydro-5-(4-hydroxy-3,5-dimethoxyphenyl)furo[3',4':6,7]naphtho[2,3-d]-1,3-dioxol-6(5aH)-one;

(5α,5aβ,8aα,9β)-9-[(4,6-O-ethylidine-β-D-glucopyranosyl)thio]-5,8,8a,9-tetrahydro-5-(4-hydroxy-3,5-dimethoxyphenyl)furo]3',4':6,7]naphtho[2,3-d]-1,3-dioxol-6-(5aH)-one.

(5α,5aβ,8aα,9β)-9-[(4,6-O-ethylidene-β-D-glucopyranosy)sulfinyl]-5,8,8a,9-tetrahydro-5-(4-hydroxy-3,5-dimethoxyphenyl)furo[3',4':6,7]naphtho[2,3-d]-1,3-dioxol-6(5aH)-one;

(5α-5aβ-8aα,9β)-9-[(4,6-O-ethylidene-β-D-glucopyranosyl)sulfonyl]-5,8,8a,9-tetrahydro-5-(4-hydroxy-3,5-dimethoxyphenyl)furo[3',4':6,7]naphtho[2,3-d)-1,3-dioxol-6-(5aH)-one;

(5α-5aβ,8aα,9β)-9-[2-(acetylamino)-2-deoxy-4,6-O-ethylidene-β-D-glucopyranosyl]thio]-5,8,8a,9-tetrahydro-5-(4-hydroxy-3,5-dimethoxyphenyl)-furo]3',4':6,7]naphtho[2,3-d]-1,3-dioxol-6(5aH)-one;

(5α,5aβ,8aα,9β)-9-[(2-amino-2-deoxy-4,6-O-ethylidene-β-D-glucopyranosyl)thio]-5,8,8a,9-tetrahydro-5-(4-hydroxy-3,5-dimethoxyphenyl)furo[3',4':6,7]naphtho[2,3-d]-1,3-dioxol-6(5aH)-one.

The novel compounds of the present invention can be prepared by reacting the 4-bromo-4'-demethylepipodophylotoxin with the appropriate alcohol or thio or metallic salt thereof. The process is preferably carried out in the presence of a polar aprotic solvent such as acetonitrile, N,N-dimethylformamide, acetone, 2-butanone, benzenenitrile, and N,N-dimethylacetamide. The process is also preferably carried out in the presence of an alkali and/or alkaline earth metal catalyst such as barium carbonate, calcium carbonate, potassium carbonate, and sodium carbonate.

The relative amounts of the 4-bromo-4'-demethylepipodophyllotoxin to the alcohol or thiol is usually about 1:1 to about 1:8 moles and preferably about 1:3 to 1:5 moles.

The reaction is usually carried out at temperatures of about −15° C. to about 80° C., typical of which being normal room temperature and is usually completed in about 1 hour to about 48 hours, typically, about 18 hours. The 4-bromo-4'-demethylepipodophyllotoxin is usually present in concentrations of about 0.02 to about 0.2 molar and preferably about 0.05 to about 0.14 molar.

The novel process of the present invention as set out above is preferably carried out in the presence of the polar solvents as set out hereinafter. However, the more preferable solvents are 2,2,2-trifluoroethanol or acetonitrile. Further, where $A_1$ is sulfur the most preferable solvent is 2,2,2-trifluoroethanol, but when $A_1$ is oxygen the most preferable solvent is acetonitrile.

In this novel process it is now advantageously found when $A_1$ is S and the solvent is 2,2,2-trifluoroethanol the reaction is nearly 100% stereospecific to the desired stereoisomer, and although when $A_1$ is oxygen and the solvent is acetonitrile the stereoselectivity of the reaction is not as specific, the resulting product provides a very favorable ratio of stereoisomers.

The reaction of this novel process is advantageously carried out at temperatures of about 0° C. to about 80° C., preferably at about 25° C.

Further, the reaction is stirred from 2 to 24 hours, providing a much preferred product, using milder conditions in considerably less time.

Although the literature provides a teaching to the use of alkyltin thiolates (see Harpp, et al., *Tetrahydron Letters* 27(4):441–444 (1986), a teaching to the effect of solvent polarity between protic and aprotic solvents (see March, *Advanced Organic Chemistry Reactions, Mechanisms and Structure*, 3rd ed., John Wiley and Sons, pp 316–320) and a teaching to the use of 2,2,2-trifluoroethanol (see Cruiekshank, et al., *Tetrahedron Letters* 26(23):2723–2726 (1985)), the present novel process provides a previously unappreciated combination of these teachings to an unexpected result.

Preparation of novel compounds of the present invention wherein R is $-S(O)_{1-2}(CH_2)_n[A(CH_2)_n]_m(-CHAH)_p-Q$ or

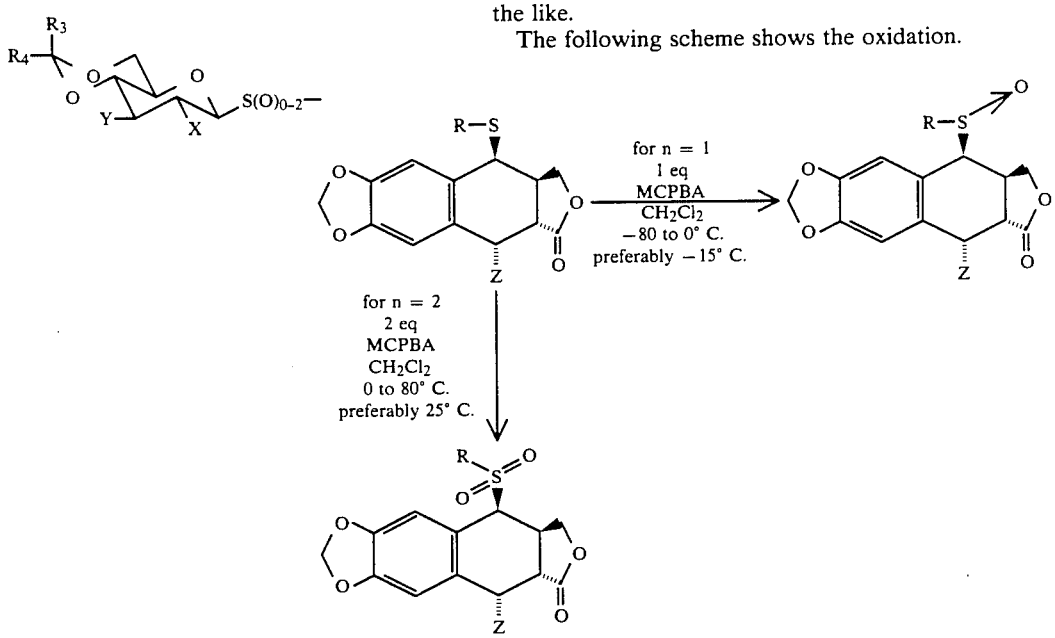

is carried out by protecting those groups known by ordinarily skilled artisans to require such protection, particularly on the novel compounds wherein groups noted to be $-S(O)_{0-2}$ are appropriately $-S-$ before further treatment.

Introduction and removal of such suitable oxygen and nitrogen protecting groups are well-known in the art of organic chemistry; see for example "Protective Groups in Organic Chemistry," J. F. W. McOmie, ed., (New York, 1973), pp 43ff, 95ff, J. F. W. McOmie, *Advances in Organic Chemistry* 3:159–190 (1963); and J. F. W. McOmie, *Chem & Ind* 603 (1979).

Examples of suitable oxygen protecting groups are benzyl, t-butyldimethylsilyl, ethoxyethyl, and the like. Protection of an N—H containing moiety is necessary for some of the processes described herein for the preparation of compounds of this invention. Suitable nitrogen protecting groups are benzyl, triphenylmethyl, trialkylsilyl, trichloroethylcarbamate, trichloroethoxycarbonyl, vinyloxycarbamate, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis, and t-butyldimethysilyl being removed by reaction with, for example, tetra-n-butyammonium fluoride.

In the processes described herein for the preparation of compounds of this invention the requirements for protective groups are generally well recognized by one skilled in the art of organic chemistry, and accordingly the use of appropriate protecting groups is necessarily implied by the processes of the charts herein, although not expressly illustrated.

The —S— group is then oxidized using oxidizing agents within the ordinary skill of the art such as MCPBA, sodium iodate, potassium permangate, and the like.

The following scheme shows the oxidation.

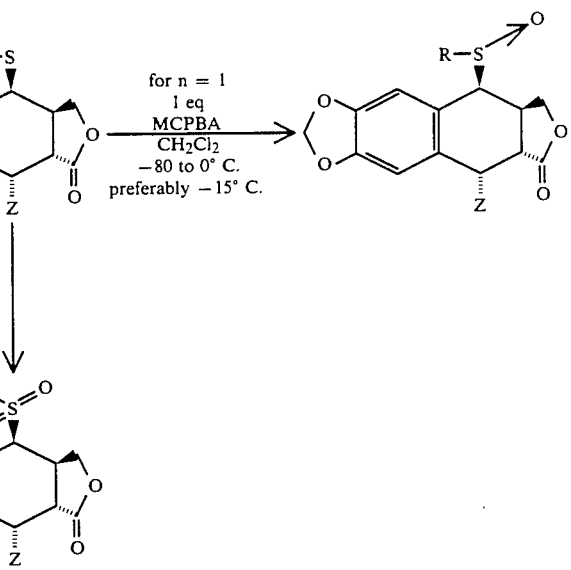

In like manner, alternatively, compounds where A is S and when R is $A-(CH_2)_n[A(CH_2)_n]_m(CHAH)_pQ$ and A of $[A(CH_2)_n]_m$ and the A of $(CHAH)_p$ may be oxidized.

One of skill in the art would recognize variations in the sequence and would recognize appropriate reaction conditions from analogous reactions which may be appropriately used in the processes to make the compounds of formula (I) herein. Further, the starting materials are known or can be prepared by known methods.

Those compounds of the present invention wherein Z is

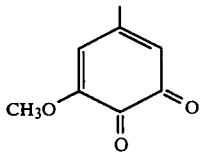

can be obtained by reacting an oxidizing agent with the compound wherein Z is

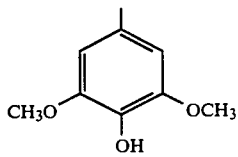

using conditions of reaction stated in PCT application publication WO86/00018, disclosure of which is incorporated herein by reference. Typical oxidizing agents include periodic acid, salts thereof such as sodium salts, lead tetraacetate, manganese dioxide, lead dioxide, oxygen, potassium nitrosodisulphonate, sodium or potassium perborate, and ferric chloride.

EXAMPLE 1

Preparation of
4-Bromo-4'-demethylepipodophyllotoxin

An about $-20°$ C. solution of about 700 ml of 1,2-dichloroethane and about 70 ml of diethyl ether is treated with about 147 g of anhydrous hydrogen bromide. The cold solution is treated with about 70.0 g (168.5 mmol) of podophyllotoxin, and the resultant solution is maintained at about $-20°$ C. for about nine days The solution is slowly brought to room temperature over about a six-hour period while being purged with a stream of dry nitrogen. The dark mixture is concentrated to a form that is triturated for about ten minutes in about 300 ml of boiling 1:1 acetone/hexanes. The solids are collected by filtration and dried to give about 59.8 g of a tan solid, mp 194°-219° C. These solids are triturated for about 45 minutes in about 500 ml of boiling 2:1 acetone:hexanes, filtered, and dried to give about 35.5 g of the product, mp 244°-251° C.

EXAMPLE 2

Preparation of
[5R-(5α,5aβ,8aα,9β)]-5,8,8a,9-tetra hydro-5-(4-hydroxy-3,5-dimethoxyphenyl)-9-[2-[2-hydroxyethyl)methylamino]ethoxy]furo[3',4':6,7]-naphtho[2,3-d]-1,3-dioxol-6(5aH)-one A mixture of about 2.0 g (4.4 mmol) of 4-bromo-4'-demethylepipodophyllotoxin obtained from the process of Example 1, about 0.84 g of barium carbonate, about 2.6 ml (22.6 mmol) of (N-methyl)diethanolamine, and about 100 ml of acetonitrile is stirred at room temperature for about 18 hours. The mixture is filtered and the filtrate is concentrated to an oil that is dissolved in chloroform. The solution is washed with water, dried over anhydrous sodium sulfate, and concentrated. The residue is triturated in ethyl acetate, the solids are collected by filtration, then dried to give 1.14 g of the product solvated with 0.4 equivalents of water, mp 183°-189° C.

EXAMPLE 3

Preparation of
[5R-(5α,5aβ,8aα,9β)]-5,8,8a,9-tetrahydro-5-(4-hydroxy-3,5-dimethoxyphenyl)-9-[2-(4morpholinyl)ethoxy]furo[3',4':6,7]naphtho[2,3-d]-1,3-dioxol-6(5aH)-one Using the Example 2, but starting with N-(2-hydroxyethyl)morpholine, the title compound solvated with 0.8 equivalents of water is prepared, mp 207°-210° C.

EXAMPLE 4

Preparation of
[5R-(5α,5aβ,8aα,9β)]-5,8,8a,9-tetrahydro-9-2-[bis(2-hydroxyethyl)amino]ethoxy]-5-(4-hydroxy-3,5-dimethoxyphenyl)furo[3'4':6,7]naphtho-2,3-d-1,3-dioxo-6(5aH)-one Using the method of Example 2, but starting with triethanolamine, the title compound solvated with 0.4 equivalents of water is prepared, mp 191°-194° C.

EXAMPLE 5

Preparation of
[5R-(5α,5aβ,8aα,9β)]-9-[2-(diethylamino)ethoxy]-5,8,8a,9-tetrahydro-5-(4-hydroxy-3,5-dimethoxyphenyl)furo[3',4':6,7]naphtho[2,3-d]-1,3-dioxol-6(5aH)-one Using the method of Example 2, but starting with N,N-diethylethanolamine, the title compound is prepared, mp 175°-181° C.

EXAMPLE 6

Preparation of
[5R-(5α,5aβ,8aα,9β)]-9-3-[(diethylamino)propoxy]-5,8,8a,9-tetrahydro-5-(4-hydroxy-3,5-dimethoxyphenyl)furo[3',4':6,7]naphtho[2,3-d]-1,3-dioxol-6(5aH)-one Using the method of Example 2, but starting with 3-diethylamino-1-propanol, the title compound is prepared, mp 160°-171° C.

EXAMPLE 7

Preparation of
[5R-(5α,5aβ,8aα,9β)]-9-[2-[2-(diethyl-amino)ethoxy]ethoxy]-5,8,8a,9-tetrahydro-5-(4-hydroxy-3,5-dimethoxyphenyl)furo[3',4':6,7]naphtho[2,3-d]-1,3-dioxol-6(5aH)-one Using the method of Example 2, but starting with 2-[2-(diethylamino)ethoxy]ethanol, the title compound solvated with 0.3 equivalents of water is prepared, mp 103°-107° C.

EXAMPLE 8

Preparation of
[5S-(5α,5aβ,8aα,9β)]-1-[2-[[5,5a,6,8,8a,9-hexahydro-9-(4-hydroxy-3,5-dimethoxyphenyl)-8-oxofuro-[3',4':6,7]naphtho[2,3-d]-1,3-dioxol-5-yl]oxy]ethyl]-2-pyrrolidinone.

Using the method of Example 2, but starting with 2-hydroxyethyl-2-pyrrolidinone, the title compound is prepared, mp 183°-188° C.

EXAMPLE 9

Preparation of
[5R-(5α,5aβ,8aα,9β)]-5,8,8a,9-tetrahydro-5-(4-hydroxy-3,5-methoxyphenyl)-9-[[2-(4-morpholinyl)ethyl]-thio]furo[3',4':6,7]naphtho[2,3-d]1,3-dioxol-6(5aH)-one Using the method of Example 2, but starting with N-(2-thioethyl)morpholine R. O. Clinton, O. J. Salvador, S. C. Laskowski, and C. M. Suler, J American Chem Soc 70:950 (1948)], the title compound is prepared after purification by chromatography on silica gel, mp 181°–184° C.

EXAMPLE 10

Preparation of
[5R-(5α,5aβ,8aα,9β)]-9-[(2,3-dihydroxypropyl)thio]-5,8,8a,9-tetrahydro-5-(4-hydroxy-3,5dimethoxyphenyl)-furo[3',4':6,7naphtho[2,3-d]-1,3-dioxol-6(5aH)-one Using the method of Example 2, but starting with thioglycerol, the title compound is prepared, mp 218°–220° C.

EXAMPLE 11

Preparation of
(5α,5aα,8aα,9β)-9-[(4,6-O-ethylidene-β-D-glucopyranosyl)thio]-5,8,8a,9-tetrahydro-5-(4-hydroxy-3,5-dimethoxyphenyl)furo[3',4':6,7]naphtho[2,3-d]-1,3-dioxol-6(5aH)-one A suspension of about 5.0 g (22.9 mmol) of 1-thio-R-D-glucose sodium salt in about 150 ml of N,N-dimethylformamide is cooled to about −10° C., then treated portionwise over about a 45-minute period with about 9.65 g (20.8 mmol) of 4-bromo-4'-demethylepipodophyllotoxin. After stirring at about −12° C. for about 2.5 hours, the solution is concentrated in a vacuum to give a foam that is dissolved in a minimum volume of hot methanol. The solution is cooled to about −30° C. and treated portionwise with about one liter of diethyl ether. The precipitated solids are collected by filtration and dried to give about 10.5 g of a white powder that shows an 81:19 ratio of diastereomers by C-8 silica gel HPLC.

A room temperature suspension of about 5.0 g (8.6 mmol) of the mixture of diastereomers in about 75 ml of dry nitromethane is treated successively with about 20 ml of acetaldehyde dimethyl acetal, and then with about 0.25 g of p-toluenesulfonic acid monohydrate. The mixture is stirred for about one hour, concentrated at about 40° C., then distributed between dichloromethane and 2% aqueous sodium bicarbonate. The dried organic layer shows two components by silica gel TLC, R$_f$=0.28 and R$_f$=0.21 (elution with 93:7:2 dichoromethane/methanol/concentrated ammonium hydroxide). The mixture is purified by flash siica gel chromatography eluting with four liters of 2% methanol in dichloromethane. Fractions containing the R$_f$=0.21 and R$_f$=0.28 components are pooled, concentrated, and crystallized from hot methanol.

The filtrate which contains the R$_f$=0.28 component is concentrated to a residue that is dissolved in a minimum volume of dichloromethane. The solution is purified by medium pressure chromatography on silica gel at ca 50 psi, utilizing gradient elution with the feeding chamber initially containing dichloromethane and the diluting chamber a 93:7:2 mixture of dichloromethane/methanol/concentrated ammonium hydroxide. Fractions containing the pure product are combined, concentrated, and crystallized from hot methanol to give about 0.29 g of the product, mp 220° C.

EXAMPLE 11A

Preparation of
(5α,5aβ,8aα,9β)-9-[(4,6-O-ethylidene-β-D-glucopyranosyl]thio]-5,8,8a,9-tetrahydro-5-(4-hydroxy-3,5-dimethoxyphenyl)furo3',4':6,7]naphtho[2,3-d]-1,3-dioxol-6(5aH)-one A suspension of about 6.18 g (28.3 mmol) of 1-thio-R-D-glucose sodium salt in about 206 ml of 2,2,2-trifluorethanol at about 25° C. under nitrogen is treated with about 8.3 ml of tri-n-butyltin chloride. The suspension is stirred at about 25° C. for about two hours, then treated with about 12 g (25.8 mmol) of 4-bromo-4'-demethylepipodophyllotoxin. The suspension is stirred overnight at about 25° C. then poured into about one liter of diethyl ether. The solids are collected by filtration then stirred as a suspension in about 600 ml of ice water for about 30 minutes. The product is collected by filtration and dried to give about 13.2 g of a white solid, mp 260° C. (decomp.) that is about 95% the 9β-diasteromer by C-8 silica gel HPLC. Recrystallization from methanol give about 9.2 g of pure 9β-diastereomer, mp 266°–268° C.

A room temperature suspension of about 5.0 g (8.6 mmol) of the pure 9β-diastereomer, about 172 mg of anhydrous 10-camphorsulfonic acid, about 21.4 ml of 1,1-dimethoxyethane, and about 74 ml of acetonitrile is stirred for about 20 hours. The clear solution is treated with about 18.6 ml of saturated aqueous sodium bicarbonate, concentrated to dryness, then distributed between dichloromethane and water. The organic phase is dried over anhydrous sodium sulfate then purified by flash silica gel chromatography eluting with 2% methanol in dichloromethane. Concentration of the product fractions followed by crystallization from methanol gives about 3.6 g of the product, mp 220° C.

EXAMPLE 12

Preparation of
(5α,5aβ,8aα,9β)-9-[(4,6-O-ethylidene-β-D-glucopyranosyl)sulfinyl]-5,8,8a,9-tetrahydro-5-(4-hydroxy-3,5-dimethoxyphenyl)furo[3',4':6,7]naphtho[2,3-d]-1,3-dioxol-6(5aH)-one A solution of about 3.6 g (5.9 mmol) of (5α,5aβ,8aα,9β)-9[(4,6-O-ethylidene-β-D-glucopyranosyl)thio]-5,8,8a,9-tetrahydro-5-(4-hydroxy-3,5-dimethoxyphenyl)furo[3',4':6,7]naphtho[2,3-d]-1,3-dioxol-6(5aH)-one in about 25 ml of dichloromethane is cooled to about −20° C., then treated successively with about 1.9 ml of pyridine and about 1.7 ml of chloroacetyl chloride. After stirring at about −20° C. for about one hour, the mixture is diluted with water. The aqueous phase is extracted twice with dichloromethane and the combined organic phases are washed with water, dried over anhydrous sodium sulfate, and concentrated to a foam. The form is purified by flash silica gel chromatography, eluting successively with dichloromethane, then 1% methanol in dichloromethane. The product fractions are combined and concentrated to give about 4.5 g of the tris-(chloroacety ester) as a foam; R$_f$=0.30 on silica gel thin layer chromatography eluting with 1% methano in dichloromethane.

A solution of about 834 mg (1.0 mmol) of the tris-(chloroacetyl ester) in about 4 ml of dichloromethane is cooled to about −15° C. and treated with about 208 mg (1 mmol) of about 80–85% m-chloroperbenzoic acid. After stirring at about −15° C. for about 1.25 hours, the solution is treated with saturated aqueous sodium bisulfite. The mixture is stirred at about 25° C. for about one hour, then the organic phase is separated and washed successively with saturated aqueous sodium bicarbonate, then water, dried over anhydrous magnesium sulfate, and concentrated to a foam. The foam is purified by flash silica gel chromatography eluting successively with dichloromethane, then 1% methanol in dichloromethane. The product fractions are combined and concentrated to give about 760 mg of the tris-(chloroacetyl ester) sulfoxide as a foam; $R_f$ on silica gel thin layer chromatography eluting with 1% methanol in dichloromethane is determined.

A solution of about 170 mg (0.2 mmol) of the tris-(chloroacetyl ester) sulfoxide in about 0.5 ml of pyridine is cooled to about 0° C. and treated with about 38 mg of ethylenediamine. After stirring for about one hour at about 0° C., the solution is diluted with water. The aqueous phase is extracted with dichloromethane and the combined organic phases are washed with brine, dried over anhydrous magnesium sulfate, and concentrated to an oil. The oil is purified by flash silica gel chromatography eluting successively with dichloromethane, 2% methanol in dichloromethane, and 4% methanol in dichloromethane. The product fractions are combined and concentrated to give about 90 mg of the product as a solid; $R_f$ on silica gel thin layer chromatography, eluting with dichloromethane:methanol:concentrated ammonium hydroxide (93:7:2) is determined; $MH^+ = 621$ mass units in fast atom bombardment spectroscopy.

EXAMPLE 13

Preparation of (5a,5aβ,8aα,9β)-9-[(4,6-O-ethylidene-β-D-glucopyranosyl)sulfonyl]-5,8,8a,9-tetrahydro-5-(4-hydroxy-3,5-dimethoxyphenyl)furo[3',4':6,7]naphtho[2,3-d]-1,3-dioxol-6(5aH)-one Reaction of about 834 (1 mmol) of the tris-(chloroacetyl ester) with about 415 mg (2 mmo) of m-chloroperbenzoic acid, as described in Example 12, at about 25° C. for about one hour followed by the same workup procedure gives about 570 mg of the tris-(chloroacetyl) ester sulfone as a foam; $R_f$ on silica gel thin layer chromatography eluting with 1% methanol in dichloromethane is determined.

Reaction of about 173 mg (0.2 mmole) of the tris-(chloroacetyl ester) sulfone with ethylenediamine followed by the same workup as described in Example 12 gives about 70 mg of the product as a solid; $R_f$ on silica gel chromatography eluting with dichloromethane:methanol:concentrated ammonium hydroxide (93:7:2) is determined. $M^+ = 636.1$ mass units in fast atom bombardment spectroscopy.

EXAMPLE 14

Preparation of (5α,5aβ,8aα,9β)-9-[[2-(acetylamino)-2-deoxy-4,6-O-ethylidene-β-D-glucopyranosyl]thio]-5,8,8a,9-tetrahydro-5-(4-hydroxy-3,5-dimethoxyphenyl)furo[3',4':6,7-]naphtho[2,3-d]-1,3-dioxol-6(5aH)-one Reaction of N-acetyl-l-thio-R-D-glucosamine sodium salt, prepared by the sodium borohydride reduction of di-(N-acetyl)-R-D-glucosaminyl)disulfide [Meyer Zu Reckendorf and Bonner, *J Org Chem* 26:4596 (1961)], with 4-bromo-4'-demethylpipodophyllotoxin followed by ethylidenation with 1,1-dimethoxethane as described in Example 11 gives the product.

EXAMPLE 15

Preparation of (5α,5aβ,8aα,9β)-9-[(2-(amino)-2-deoxy-4,6-O-ethylidene-β-D-glucopyranosyl]thio]-5,8,8a,9-tetrahydro-5-(4-hydroxy-3,5-dimethoxyphenyl)-furo-[3',4':6,7]naphtho[2,3-d]-1,3-dioxol-6(5aH)-one Reaction of the title compound of Example 14 with about one equivalent of triethylononium fluoroborate followed by hydrolysis of the intermediate O-ethyl acetamidium fluoroborate with water gives the product.

Compounds of the present invention are tested for antineoplastic activity by the following in vitro L1210 and in vivo P388 leukemia protocols:

In Vitro Antineoplastic Test Protocol

The activities of compounds of the present invention are tested against the L1210 murine leukemia cell line in vitro.

Lizio cells are grown in RPMI 1640 culture medium containing 10% fetal bovine serum and gentamicin (50 micrograms per milliliter). A stock solution of the test compound is prepared in the appropriate solvent and further diluted in culture medium. Sequential twofold dilutions of drug are performed with 50 microliter transfers in 96-well microliter plates followed by the addition of 50 microliters of cell suspension containing $4 \times 10^4$ cells per milliliter.

After incubation at 37° C. in a humidified atmosphere of 5% $CO_2$ in air for three days, 10 microliters of MTT [5 milligrams/milliliter 3-(4,5-dimethyl-2-thiazol)-2,5-diphenyltetrazolium bromide] are added to each well and the plates incubated at 37° C. for 3 hours before the addition of 100 microliters of 0.15 N HCl in isopropanol. Absorbance is read within one hour on a Dynatech MR 600 plate reader at 2 test wavelength of 570 nm and a reference wavelength of 630 nm. A microcomputer program converts optical density readings to percent growth and determines $IC_{50}$ values (the amount of drug required to reduce absorbance to 50% of untreated controls) using nonlinear regression analysis.

In Vivo Antineoplastic Test Protocol

The activities of compounds of the present invention are tested against the P388 murine leukemia cell line in vivo. This protocol tests the effectiveness of a given compounds to inhibit the growth of the transplanted P388 murine leukemia cell line in male and female CD2F1 mice. Each test included a group of six or seven mice. The test is described in detail in *Cancer Chemotherapy Reports*, Part 3, Volume 3, pp 1–85 (1972).

The tumor cell line is transplanted into the test animals by intraperitoneal injection of ascites fluid containing the cell line. The test compounds are administered to the test animals intraperitoneally once daily for five consecutive days at various doses following tumor inoculation. The animals are weighed and survivors are recorded on a regular basis for 40 days.

A compound is designated "toxic" if, at a given dose, no animal survives after four days following first injection of the test compound. A ratio of survival time for treated animals (T) animals relative to control (C) animals is calculated for each nontoxic dose. A criterion for efficacy is a ratio of (T/C)×100 equal to or greater than 125.

The results of these tests are reported in the table below for the compounds represented by the following formula:

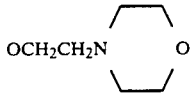

| Example No. | R | L1210 Leukemia in Vitro Mean IC$_{50}$ (μM) | P388 Leukemia In Vitro Dose (mg/kg/inj) | % T/C (40-day) survivors |
|---|---|---|---|---|
| 2 | OCH$_2$CH$_2$N(CH$_3$)CH$_2$CH$_2$OH | .103 | 0.38 | 170 |
| 3 | OCH$_2$CH$_2$N⟨morpholine⟩ | .235 | 3.1 | 179 |
| 4 | OCH$_2$CH$_2$N(CH$_2$CH$_2$OH)$_2$ | .336 | 1.5 | 160 |
| 5 | OCH$_2$CH$_2$NEt$_2$ | .198 | 3.1 | 140 |
| 6 | OCH$_2$CH$_2$NEt$_2$ | .250 | 2.0 | 137 |
| 7 | OCH$_2$CH$_2$OCH$_2$CH$_2$NEt$_2$ | .253 | 50 | 170 |
| 8 | OCH$_2$CH$_2$N⟨pyrrolidinone⟩ | .50 | 100 | 167 |
| 9 | SCH$_2$CH$_2$N⟨morpholine⟩ | 1.39 | 50 | 127 |
| 10 | SCH$_2$CH(OH)CH$_2$OH | .767 | 12.5 | 114 |
| 11 | (thiosugar structure) | .305 | 50 | 182 (3/6) |
| Prior Art | Etoposide | | 40$^a$ | 295 (4/10)$^b$ |

$^a$Administered once daily on Days 1, 5, and 9, following tumor implantation.
$^b$60-days survivors.

The above data illustrates that the new compounds of the present invention are active antitumor agents and exhibit good potency. The compounds of Example 11 is highly active. In addition, compounds of the present invention exhibit high solubility in water.

We claim:
1. A compound of formula (I)

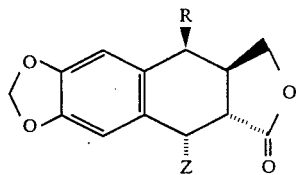

wherein A is A—(CH$_2$)$_n$[A(CH$_2$)$_n$]$_m$(CHAH)$_p$—O or

each A, independently, is O, S, SO, or SO$_2$; n is an integer from 1 to 6, except when m and p, taken together, are zero, then n is 2 to 6; m is 0, 1, or 2; p is 0, 1, or 2; Q is H, or alkyl from 1 to 6 carbon atoms which may be substituted with an NR$_1$R$_2$ group wherein each R$_1$ and R$_2$, independently, is selected from the group consisting of H, alkyl containing 1 to 6 carbon atoms which may be substituted with OH, or alkanoyl containing 1 to 6 carbon atoms, or R$_1$ and R$_2$ are interconnected and together with the N to which they are connected form an N heterocyclic ring of 5 to 6 carbon atoms; R$_3$ is hydrogen, and R$_4$ is an alkyl, alkenyl, cycloalkyl, 2-furyl, 2-thienyl, aryl, aralkyl, or aralkenyl, wherein the aromatic ring may optionally be substituted by one or more of hydroxyl, alkyl, alkoxy, nitro, or halogen radicals; or R$_3$ and R$_4$ together with the carbon atom to which they are attached may form saturated cycloaliphatic ring having 5 or 6 carbon atoms; each X and Y, individually, is OH or NR$_6$R$_7$ wherein each R$_6$ and R$_7$, independently, is H, alkyl containing 1 to 6 carbon atoms, or one of R$_6$ and R$_7$ is acyl; and Z is

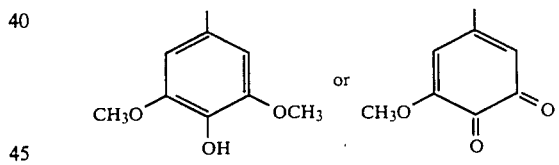

2. The compound of claim 1 wherein R is

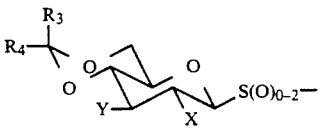

wherein the substituents R$_3$, R$_4$, X and Y are defined as in claim 1.

3. The compound of claim 1 wherein R is A(CH$_2$)$_n$[A(CH$_2$)$_n$]$_m$(CHAH)$_p$Q wherein the substituents A, n, m, p and Q are as defined in claim 1.

4. The compound of claim 3 wherein each A is O.

5. The compound of claim 3 wherein each A is S or S(O)$_{1-2}$.

6. The compound of claim 1 being [5R-(5α,5aβ,8aα,9β)]-5,8,8a,9-tetrahydro-5-(4-hydroxy-3,5-dimethoxyphenyl)-9-[2-[(2-hydroxyethyl)methylamino]ethoxy]-furo[3',4':6,7]naphtho[2,3-d]-1,3-dioxol-6(5aH)-one.

7. The compound of claim 1 being [5R-(5α,5aβ,8aα,9β)]-5,8,8a,9-tetrahydro-5-(4-hydroxy -3,5-dimethoxyphenyl)-9-[2-(4-morpholinyl)ethoxy]-5-(4-hydroxy-3,5-dimethoxyphenyl)furo[3',4':6,7]naphtho-[2,3-d]-1,3-dioxol-6(5aH)-one.

8. The compound of claim 1 being [5R-(5α,5aβ,8aα,9β)]-5,8,8a,9-tetrahydro-9-[2-[bis(2-hydroxyethyl)amino]ethoxy]-5-(4-hydroxy-3,5-dimethoxyphenyl)furo[3',4':6,7]-naphtho[2,3-d]-1,3-dioxol-6(5aH)one.

9. The compound of claim 1 being [5R-(5α,5aβ,8aα,9β)]-9-2-(diethylamino)ethoxy]-5,8,8a,9-tetrahydro-5-(4-hydroxy-3,5-dimethoxyphenyl)-furo[3',4':6,7]-naphtho[2,3-d]-1,3-dioxol-6(5aH)-one.

10. The compound of claim 1 being [5R-(5α,5aβ,8aα,9β)]-9-[3-[(diethylamino)propoxy]-5,8,8a,9-tetrahydro-5-(4-hydroxy-3,5-dimethoxyphenyl)furo[3',4':6,7]-naphtho[2,3-d]-1,3-dioxol-6(5aH)-one.

11. The compound of claim 1 being [5R-(5α,5aβ,8aα,9β)]-9-[2-[2-(diethylamino)ethoxy]ethoxy]-5,8,8a,9-tetrahydro-5-(4-hydroxy-3,5-dimethoxyphenyl)furo-[3',4':6,7]naphtho[2,3-d]-1,3-dioxol-6(5aH)-one.

12. The compound of claim 1 being [5S-(5α,5aα,8aα,9β)]-1-[2-[[5,5a,6,8,8a,9-hexahydro-9-(4-hydroxy-3,5-dimethoxyphenyl)-8-oxofuro[3',4':6,7]naphtho-[2,3-d]-1,3-dioxol-5-yl]oxy]ethyl]-2-pyrrolidinone.

13. The compound of claim 1 being [5R-(5α,5aβ,8aα,9β)]-5,8,8a,9-tetrahydro-5-(4-hydroxy-3,5-dimethoxyphenyl)-9-[[2-(4-morpholinyl)ethyl]thio]furo-[3',4':6,7]naphtho[2,3-d]-1,3-dioxol-6(5aH)-one.

14. The compound of claim 1 being [5R-(5α,5aβ,8aα,9β)]-9-[(2,3-dihydroxypropyl)thio]-5,8,8a,9-tetrahydro-5-(4-hydroxy-3,5-dimethoxypheny-1)furo[3',4':6,7]-naphtho[2,3-d]-1,3-dioxol-6(5aH)-one.

15. The compound of claim 2 being (5α,5aβ,8aα,9β)-9-[(4,6-O-ethyylidene-β-D-glucopyranosyl)thio]-5,8,8a,9-tetrahydro-5-(4-hydroxy-3,5-dimethoxyphenyl)furo[3',4':6,7]naphtho[2,3-d]-1,3-dioxol-6(5aH)-one.

16. The compound of claim 2 being (5α,5aβ,s8aα,9β)-9-[(4,6-O-ethylidene-β-D-glucopyranosyl)sulfinyl]-5,8,8a,9-tetrahydro-5-(4-hydroxy-3,5-dimethoxyphenyl)furo[3',4':6,7]naphtho[2,3-d]-1,3-dioxol-6(5aH)-one.

17. The compound of claim 2 being (5α,5aβ,8aα,9β)-9-[(4,6-O-ethylidene-β-D-glucopyranosyl)sulfonyl]-5,8,8a,9-tetrahydro-5-(4-hydroxy-3,5-dimethoxyphenyl)furo[3',4':6,7]naphtho[2,3-d]-1,3-dioxol-6(5aH)-one.

18. The compound of claim 2 wherein one of X and Y is $NR_6R_7$, wherein each $R_6$ and $R_7$, independently, is H, alkyl containing 1 to 6 carbon atoms, or one of $R_6$ and $R_7$ is acyl.

19. The compound of claim 18 being (5α,5aβ,8aα,9β)-9-[[2-(acetylamino)-2-deoxy-4,6-O-ethylidene-β-D-glucopyranosyl]thio]-5,8,8a,9-tetrahydro-5-(4-hydroxy-3,5-dimethoxyphenyl)furo[3',4':6,7]-naphtho[2,3-d]-1,3-dioxol-6(5aH)-one.

20. The compound of claim 18 being (5α,5aβ,8aα,9β)-9-[(2-amino-2-deoxy-4,6-O-ethylidene-β-D-glucopyranosyl)thio]-5,8,8a,9-tetrahydro-5-(4-hydroxy-3,5-dimethoxyphenyl)furo[3',4':6,7]-naphtho[2,3-d]-1,3-dioxol-6(5aH)-one.

* * * * *

UNITED STATES PATENT AND TRADEMARK OFFICE
CERTIFICATE OF CORRECTION

Patent No: 5,061,791
Dated: October 29, 1991
Inventor(s): Showalter, et al.

It is certified that error appears in the above-identified patent and that said Letters Patent is hereby corrected as shown below:

Column 16, line 10, the "A" after "wherein" should be "R" and "O" should be "Q"

Signed and Sealed this

Sixteenth Day of March, 1993

Attest:

STEPHEN G. KUNIN

Attesting Officer

Acting Commissioner of Patents and Trademarks